US 6,520,919 B1

(12) United States Patent
Nunome et al.

(10) Patent No.: US 6,520,919 B1
(45) Date of Patent: Feb. 18, 2003

(54) INFERIOR-AND-SUPERIOR-LIMB BLOOD-PRESSURE-INDEX MEASURING APPARATUS

(75) Inventors: Tomohiro Nunome, Komaki (JP); Hideo Nishibayashi, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 10/180,338

(22) Filed: Jun. 27, 2002

(30) Foreign Application Priority Data

Jan. 9, 2002 (JP) ........................................ 2002-002194

(51) Int. Cl.[7] .............................................. A61B 5/00
(52) U.S. Cl. ........................ 600/494; 600/490; 600/495
(58) Field of Search ................................. 600/485, 490, 600/493–6, 500, 503

(56) References Cited

U.S. PATENT DOCUMENTS

| | | | |
|---|---|---|---|
| 6,332,869 B1 | | 12/2001 | Ogura et al. |
| 6,355,000 B1 | * | 3/2002 | Ogura ........................... 60/490 |
| 6,379,309 B1 | * | 4/2002 | Ogura et al. ................. 600/490 |
| 6,440,079 B1 | * | 8/2002 | Ogura et al. ................. 600/493 |

FOREIGN PATENT DOCUMENTS

JP    B1 3027751    1/2000

\* cited by examiner

Primary Examiner—Robert L. Nasser
(74) Attorney, Agent, or Firm—Oliff & Berridge, PLC (57) ABSTRACT

An apparatus for measuring an inferior-and-superior-limb blood-pressure index of a living subject, including an inferior-limb blood-pressure measuring device, a superior-limb blood-pressure measuring device, an index determining means for determining the inferior-and-superior-limb blood-pressure index, based on a systolic blood pressure of an inferior limb, measured by the inferior-limb blood-pressure measuring device and a systolic blood pressure of a superior limb, measured by the superior-limb blood-pressure measuring device, an estimated-inferior-limb-systolic-blood-pressure determining means for determining an estimated systolic blood pressure of the inferior limb, an estimated-superior-limb-systolic-blood-pressure determining means for determining an estimated systolic blood pressure of the superior limb, and a cuff-pressure control means for controlling at least one of respective pressures of the inferior-limb cuff and the superior-limb cuff, such that when the respective pressures of an inferior-limb cuff and a superior-limb cuff are decreased, the respective pressures of the inferior-limb cuff and the superior-limb cuff become equal to the respective estimated systolic blood pressures of the inferior limb and the superior limb, at the same time.

7 Claims, 7 Drawing Sheets

** INFERIOR-AND-SUPERIOR-LIMB BLOOD-PRESSURE-INDEX MEASURING APPARATUS

BACKGROUND OF THE INVENTION

1. Field of the Invention

The present invention relates to an inferior-and-superior-limb blood-pressure-index measuring apparatus for measuring an inferior-and-superior-limb blood-pressure index of a living subject.

2. Related Art Statement

An inferior-and-superior-limb blood-pressure index is generally known as a ratio of a blood pressure of a superior limb of a living subject to a blood pressure of an inferior limb of the subject, or a ratio of the blood pressure of the inferior limb to that of the superior limb. Respective systolic blood pressures of the inferior and superior limbs are generally used as the respective blood pressures of those limbs. In addition, generally, an ankle is selected as the inferior limb and an upper arm is selected as the superior limb, so that an ankle-and-upper-arm blood-pressure index is determined as the inferior-and-superior-limb blood-pressure index. The inferior-and-superior-limb blood-pressure index represented by the ankle-and-upper-arm blood-pressure index is used as an index useful for making a diagnosis about stenosis or obliteration caused by atherosclerosis.

Since the inferior-and-superior-limb blood-pressure index is a simple ratio, i.e., a ratio of one of inferior-limb blood pressure and superior-limb blood pressure to the other, a diagnosis made based on the index is largely influenced by a small change of the inferior-limb and/or superior-limb blood pressure. Meanwhile, blood pressure of a living person may largely change in a short time. For example, even when the person is resting, his or her blood pressure may physiologically change by more than 20 mmHg in 10 seconds. Therefore, if an inferior-limb blood pressure and a superior-limb blood pressure are measured at different times, blood pressure of the person may largely change between those times. Thus, measurement of a reliable inferior-and-superior-limb blood-pressure index requires that an inferior-limb blood pressure and a superior-limb blood pressure be measured at substantially the same time.

Japanese Patent No. 3,027,751 or its corresponding U.S. Pat. No. 6,332,869 discloses an ankle-and-upper-arm blood-pressure-index measuring apparatus which measures an ankle systolic blood pressure and an upper-arm systolic blood pressure at substantially the same time, and calculates an ankle-and-upper-arm blood-pressure index based on the thus measured ankle and upper-arm systolic blood pressure. The disclosed apparatus measures the ankle and upper-arm systolic blood pressure at substantially the same time, by carrying out two blood-pressure measuring operations. More specifically described, the apparatus includes an ankle cuff wound around an ankle and an upper-arm cuff wound around an upper arm, determines the ankle and upper-arm systolic blood pressure obtained in the first blood-pressure measuring operation, as estimated ankle and upper-arm systolic blood pressure, respectively, and controls, in the second blood-pressure measuring operation, the respective pressures of the ankle cuff and the upper-arm cuff, such that the respective pressures of the ankle cuff and the upper-arm cuff become equal to the estimated ankle and upper-arm systolic blood pressure, respectively, at substantially the same time.

However, since the ankle-and-upper-arm blood-pressure-index measuring apparatus disclosed in the above-identified document needs to carry out two blood-pressure measuring operations, it takes a long time to measure the blood-pressure index and a patient feels much discomfort caused by pressing of the cuffs.

SUMMARY OF THE INVENTION

It is therefore an object of the present invention to provide an inferior-and-superior-limb blood-pressure-index measuring apparatus which can measure, in a single blood-pressure measuring operation, an inferior-limb systolic blood pressure and a superior-limb systolic blood pressure of a patient, at substantially the same time, and thus can measure an inferior-and-superior-limb blood-pressure index of the patient in a short time with reduced discomfort felt by the patient.

The above object has been achieved by the present invention. According to the present invention, there is provided an apparatus for measuring an inferior-and-superior-limb blood-pressure index of a living subject, comprising an inferior-limb blood-pressure measuring device which includes an inferior-limb cuff adapted to be wound around a portion of an inferior limb of the subject and measures a systolic blood pressure of the inferior limb based on a heartbeat-synchronous signal which is obtained from the subject when a pressure of the inferior-limb cuff is decreased after the pressure of the inferior-limb cuff is increased up to an estimated pressure higher than a systolic blood pressure of the portion of the inferior limb; a superior-limb blood-pressure measuring device which includes a superior-limb cuff adapted to be wound around a portion of a superior limb of the subject and measures a systolic blood pressure of the superior limb based on a heartbeat-synchronous signal which is obtained from the subject when a pressure of the superior-limb cuff is decreased after the pressure of the superior-limb cuff is increased up to a pressure higher than an estimated systolic blood pressure of the portion of the superior limb; an inferior-and-superior-limb-blood-pressure-index determining means for determining the inferior-and-superior-limb blood-pressure index of the subject, based on the systolic blood pressure of the inferior limb measured by the inferior-limb blood-pressure measuring device and the systolic blood pressure of the superior limb measured by the superior-limb blood-pressure measuring device; an estimated-inferior-limb-systolic-blood-pressure determining means for determining the estimated systolic blood pressure of the portion of the inferior limb based on a heartbeat-synchronous signal which is obtained from the subject when the pressure of the inferior-limb cuff is increased; an estimated-superior-limb-systolic-blood-pressure determining means for determining the estimated systolic blood pressure of the portion of the superior limb based on a heartbeat-synchronous signal which is obtained from the subject when the pressure of the superior-limb cuff is increased; and a cuff-pressure control means for controlling at least one of the respective pressures of the inferior-limb cuff and the superior-limb cuff, such that when the respective pressures of the inferior-limb cuff and the superior-limb cuff are decreased, the respective pressures of the inferior-limb cuff and the superior-limb cuff become equal to the respective estimated systolic blood pressures of the inferior limb and the superior limb, at a same time.

According to this invention, the estimated-inferior-limb-systolic-blood-pressure determining means determines the estimated systolic blood pressure of the inferior limb based on the heartbeat-synchronous signal obtained when the pressure of the inferior-limb cuff is increased, and the estimated-superior-limb-systolic-blood-pressure determining means determines the estimated systolic blood pressure of the superior limb based on the heartbeat-synchronous signal obtained when the pressure of the superior-limb cuff is increased. When the respective pressures of the inferior-limb and superior-limb cuffs are slowly decreased after being increased, the cuff-pressure control means controls at least one of the respective pressures of the inferior-limb cuff and the superior-limb cuff, such that the respective pressures of the inferior-limb cuff and the superior-limb cuff become equal to the respective estimated systolic blood pressures of the inferior limb and the superior limb, at the same time. Thus, the present apparatus can measure, in the single blood-pressure measuring operation, the inferior-limb systolic blood pressure and the superior-limb systolic blood pressure, at substantially the same time.

Here, preferably, the cuff-pressure control means comprises a pressure-increase control means for increasing the pressure of the inferior-limb cuff from a pressure which is estimated to be lower than a diastolic blood pressure of the portion of the inferior limb, and increasing the pressure of the superior-limb cuff from a pressure which is estimated to be lower than a diastolic blood pressure of the portion of the superior limb, wherein the apparatus further comprises a diastolic-and-mean-blood-pressure measuring device which measures a diastolic blood pressure and a mean blood pressure of the inferior limb based on the heartbeat-synchronous signal obtained from the subject when the pressure of the inferior-limb cuff is increased by the pressure-increase control means, and measures a diastolic blood pressure and a mean blood pressure of the superior limb based on the heartbeat-synchronous signal obtained from the subject when the pressure of the superior-limb cuff is increased by the pressure-increase control means; an inferior-limb-pulse-wave detecting device which detects an inferior-limb pulse wave that is an oscillation of the pressure of the inferior-limb cuff a superior-limb-pulse-wave detecting device which detects a superior-limb pulse wave that is an oscillation of the pressure of the superior-limb cuff; an inferior-limb-pulse-wave-magnitude determining means for determining a minimal magnitude, an area-gravity-center magnitude, and a maximal magnitude of at least one heartbeat-synchronous pulse of the inferior-limb pulse wave detected by the inferior-limb-pulse-wave detecting device in a state in which the pressure of the inferior-limb cuff is kept at a pressure which is estimated to be lower than a mean blood pressure of the portion of the inferior limb; and a superior-limb-pulse-wave-magnitude determining means for determining a minimal magnitude, an area-gravity-center magnitude, and a maximal magnitude of at least one heartbeat-synchronous pulse of the superior-limb pulse wave detected by the superior-limb-pulse-wave detecting device in a state in which the pressure of the superior-limb cuff is kept at a pressure which is estimated to be lower than a mean blood pressure of the portion of the superior limb, and wherein the estimated-inferior-limb-systolic-blood-pressure determining means determines the estimated systolic blood pressure of the portion of the inferior limb based on the diastolic blood pressure and the mean blood pressure of the inferior limb, measured by the systolic-and-mean-blood-pressure measuring device, and the minimal magnitude, the area-gravity-center magnitude, and the maximal magnitude of the inferior limb pulse wave, determined by the inferior-limb-pulse-wave-magnitude determining means, and the estimated-superior-limb-systolic-blood-pressure determining means determines the estimated systolic blood pressure of the portion of the superior limb based on the diastolic blood pressure and the mean blood pressure of the superior limb, measured by the systolic-and-mean-blood-pressure measuring device, and the minimal magnitude, the area-gravity-center magnitude, and the maximal magnitude of the superior-limb pulse wave, determined by the superior-limb-pulse-wave-magnitude determining means.

According to this feature, when the pressure-increase control means slowly increases the respective pressures of the inferior-limb cuff and the superior-limb cuff, the inferior-limb-pulse-wave detecting device detects the inferior-limb pulse wave, the superior-limb-pulse-wave detecting device detects the superior-limb pulse wave, and the diastolic-and-mean-blood-pressure measuring device measures the diastolic and mean blood pressure of the inferior limb, and the diastolic and mean blood pressure of the superior limb. And, the estimated-inferior-limb-systolic-blood-pressure determining means determines the estimated systolic blood pressure of the inferior limb based on the diastolic and mean blood pressure of the inferior limb, actually measured by the systolic-and-mean-blood-pressure measuring device, and a minimal magnitude, an area-gravity-center magnitude, and a maximal magnitude of the inferior-limb pulse wave actually detected, and the estimated-superior-limb-systolic-blood-pressure determining means determines the estimated systolic blood pressure of the superior limb based on the diastolic and mean blood pressure of the superior limb, actually measured by the systolic-and-mean-blood-pressure measuring device, and a minimal magnitude, an area-gravity-center magnitude, and a maximal magnitude of the superior-limb pulse wave actually detected. Therefore, the present apparatus can determine, with high accuracy, the estimated systolic blood pressure of the inferior limb and the estimated systolic blood pressure of the superior limb, and accordingly can measure, in the single blood-pressure measuring operation, the inferior-limb systolic blood pressure and the superior-limb systolic blood pressure, at accurately the same time.

In addition, preferably, the inferior-and-superior-limb blood-pressure-index measuring apparatus further comprises a mean-blood-pressure measuring device which measures a mean blood pressure of the inferior limb based on the heartbeat-synchronous signal obtained from the subject when the pressure of the inferior-limb cuff is increased, and measures a mean blood pressure of the superior limb based on the heartbeat-synchronous signal obtained from the subject when the pressure of the superior-limb cuff is increased, wherein the estimated-inferior-limb-systolic-blood-pressure determining means determines the estimated systolic blood pressure of the portion of the inferior limb based on the heartbeat-synchronous signal obtained from the subject when the pressure of the inferior-limb cuff is increased and before the mean blood pressure of the inferior limb is measured by the mean-blood-pressure measuring device, wherein the estimated-superior-limb-systolic-blood-pressure determining means determines the estimated systolic blood pressure of the portion of the superior limb based on the heartbeat-synchronous signal obtained from the subject when the pressure of the superior-limb cuff is increased and before the mean blood pressure of the superior limb is measured by the mean-blood-pressure measuring device, and wherein the cuff-pressure control means comprises a pressure-increase control means for increasing, at a first rate, the pressure of the inferior-limb cuff from a pressure which is estimated to be lower than a diastolic blood pressure of the portion of the inferior limb, and increasing, at a second rate, the pressure of the superior-limb cuff from a pressure which is estimated to be lower than a diastolic blood pressure of the portion of the superior limb, and further increasing, at a third rate higher than the first rate, the pressure of the inferior-limb cuff to a first pressure-decrease starting pressure determined based on the estimated systolic blood pressure of the inferior limb determined by the estimated-inferior-limb-systolic-blood-pressure determining means, when the mean blood pressure of the inferior limb is measured by the mean-blood-pressure measuring device, at a time later than a time when the mean blood pressure of the superior limb is measured by the mean-blood-pressure measuring device, and further increasing, at a fourth rate higher than the second rate, the pressure of the superior-limb cuff to a second pressure-decrease starting pressure determined based on the estimated systolic blood pressure of the superior limb determined by the estimated-superior-limb-systolic-blood-pressure determining means, when the mean blood pressure of the superior limb is measured at a time later than a time when the mean blood pressure of the inferior limb is measured.

According to this feature, when the pressure-increase control means slowly increases the respective pressures of the inferior-limb cuff and the superior-limb cuff, the mean-blood-pressure measuring device measures the mean blood pressure of the inferior limb and the mean blood pressure of the superior limb. The estimated-inferior-limb-systolic-blood-pressure determining means determines the estimated systolic blood pressure of the inferior limb based on the heartbeat-synchronous signal obtained before the mean blood pressure of the inferior limb is measured, and the estimated-superior-limb-systolic-blood-pressure determining means determines the estimated systolic blood pressure of the superior limb based on the heartbeat-synchronous signal obtained before the mean blood pressure of the superior limb is measured. And, the pressure-increase control means further increases, more quickly, the pressure of the inferior-limb cuff to a pressure-decrease starting pressure determined based on the estimated systolic blood pressure of the inferior limb, when the mean blood pressure of the inferior limb is measured at a time later than a time when the mean blood pressure of the superior limb is measured, and further increases, more quickly, the pressure of the superior-limb cuff to a pressure-decrease starting pressure determined based on the estimated systolic blood pressure of the superior limb, when the mean blood pressure of the superior limb is measured at a time later than a time when the mean blood pressure of the inferior limb is measured. Thus, the present apparatus can increase the respective pressures of the inferior-limb cuff and the superior-limb cuff, to the respective pressure-decrease starting pressures, in a shorter time than a time in which the respective pressures of the inferior-limb cuff and the superior-limb cuff are slowly increased till respective systolic blood pressures of the inferior and superior limbs are measured so that those measured systolic blood pressures of the inferior and superior limbs are used as respective estimated systolic blood pressures of the inferior and superior limbs.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
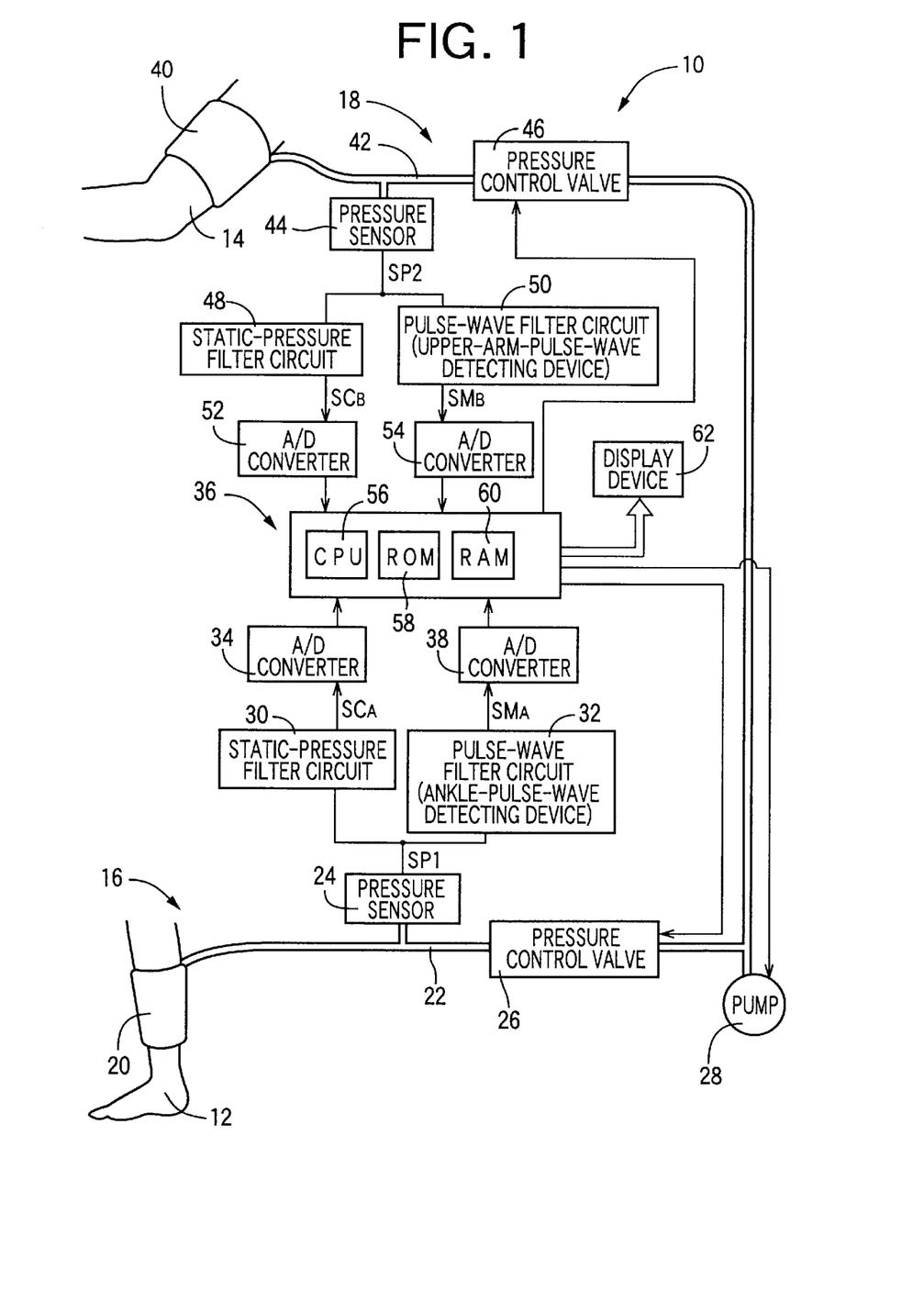
FIG. 1 is a diagrammatic view for explaining a construction of an ankle-and-upper-arm blood-pressure-index measuring apparatus to which the present invention is applied.

Hereinafter, there will be described a preferred embodiment of the present invention in detail by reference to the drawings. FIG. 1 is a diagrammatic view for explaining a construction of an ankle-and-upper-arm blood-pressure-index measuring apparatus 10 to which the present invention is applied. The ankle-and-upper-arm blood-pressure-index measuring apparatus 10, shown in FIG. 1, functions as an inferior-and-superior-limb blood-pressure-index measuring apparatus wherein an ankle 12 is selected as an inferior limb and an upper arm 14 is selected as a superior limb. The present apparatus 10 carries out measurements on a patient as a living subject who takes a face-down, a lateral, or a face-up position so that the upper arm and ankle of the patient are substantially level with each other.

In FIG. 1, the ankle-and-upper-arm blood-pressure (BP) index measuring apparatus 10 includes an ankle BP measuring device 16 which measures a BP value of the ankle 12 (e.g., a right ankle) and which functions as an inferior-limb BP measuring device, and an upper-arm BP measuring device 18 which measures a BP value of the upper arm 14 and functions as a superior-limb BP measuring device.

The ankle BP measuring device 16 includes an ankle cuff 20 which includes a belt-like cloth bag and a rubber bag accommodated in the cloth bag and which is adapted to be wound around the ankle 12 of the patient; a piping 22; and a pressure sensor 24, a pressure control valve 26, and an air pump 28 which are connected to the ankle cuff 20 via the piping 22. The pressure control valve 26 adjusts a pressure of a pressurized air supplied from the air pump 28, and supplies the pressure-adjusted air to the ankle cuff 20, or discharges the pressurized air from the ankle cuff 22, so as to control an air pressure in the ankle cuff 20.

The pressure sensor 24 detects the air pressure in the ankle cuff 20, and supplies a pressure signal, SP1, representing the detected air pressure, to a static-pressure filter circuit 30 and a pulse-wave filter circuit 32. The static-pressure filter circuit 30 includes a low-pass filter which extracts, from the pressure signal SP1, an ankle-cuff-pressure signal, $SC_A$, representing a static component of the detected air pressure, i.e., a pressing pressure of the ankle cuff 20 (hereinafter, referred to as the ankle-cuff pressure, $PC_A$). The filter circuit 30 supplies the ankle-cuff-pressure signal $SC_A$ to an electronic control device 36 via an A/D (analog-to-digital) converter 34.

The pulse-wave filter circuit 32 includes a band-pass filter which extracts, from the pressure signal SP1, an anklepulse-wave signal, $SM_A$, representing an ankle pulse wave as an oscillatory component of the detected air pressure that has prescribed frequencies. The filter circuit 32 supplies the ankle-pulse-wave signal $SM_A$ to the control device 36 via an A/D converter 38. Since the ankle pulse wave indicates the oscillation of pressure of the ankle cuff 20, the filter circuit 32 functions as an ankle-pulse-wave detecting device or an inferior-limb-pulse-wave detecting device.

The upper-arm BP measuring device 18 includes an upper-arm cuff 40 having a construction identical with that of the cuff of the ankle BP measuring device 16; and a piping 42, a pressure sensor 44, and a pressure control valve 46. The upper-arm cuff 40 is wound around the upper arm 14. The pressure control valve 46 is connected to the air pump 28. The pressure sensor 44 detects an air pressure in the upper-arm cuff 40, and supplies a pressure signal, SP2, representing the detected air pressure, to a static-pressure filter circuit 48 and a pulse-wave filter circuit 50 which have respective constructions identical with those of the counterparts of the ankle BP measuring device 16. The static-pressure filter circuit 48 extracts, from the pressure signal SP2, an upper-arm-cuff-pressure signal, $SC_B$, representing a static component of the detected air pressure, i.e., a pressing pressure of the upper-arm cuff 40 (hereinafter, referred to as the upper-arm-cuff pressure, $PC_B$). The filter circuit 48 supplies the upper-arm-cuff-pressure signal $SC_B$ to the control device 36 via an A/D converter 52. The pulse-wave filter circuit 50 extracts, from the pressure signal SP2, an upper-arm-pulse-wave signal, $SM_B$, representing an upper-arm pulse wave as an oscillatory component of the detected air pressure that has prescribed frequencies. The filter circuit 50 supplies the upper-arm-pulse-wave signal $SM_B$ to the control device 36 via an A/D converter 54. Since the upper-arm pulse wave indicates the oscillation of pressure of the upper-arm cuff 40, the filter circuit 50 functions as an upper-arm-pulse-wave detecting device or a superior-limb-pulse-wave detecting device.

The control device 36 is essentially provided by a microcomputer including a CPU (central processing unit) 56, a ROM (read only memory) 58, a RAM (random access memory) 60, and an I/O (input-and-output) port, not shown, and the CPU 56 processes signals according to the programs pre-stored in the ROM 58, while utilizing the data-storing function of the RAM 60. The control device 36 outputs, from the I/O port, drive signals to the air pump 28 and the two pressure control valves 26, 46 so as to control the respective operations thereof and thereby control the respective air pressures of the ankle cuff 20 and the upper-arm cuff 40. In addition, the CPU 56 processes signals supplied to the control device 36, so as to determine an ankle-and-upper-arm BP index (hereinafter, referred to as an ABI value) and control a display device 62 to display the thus determined ABI value.

Figure 2:
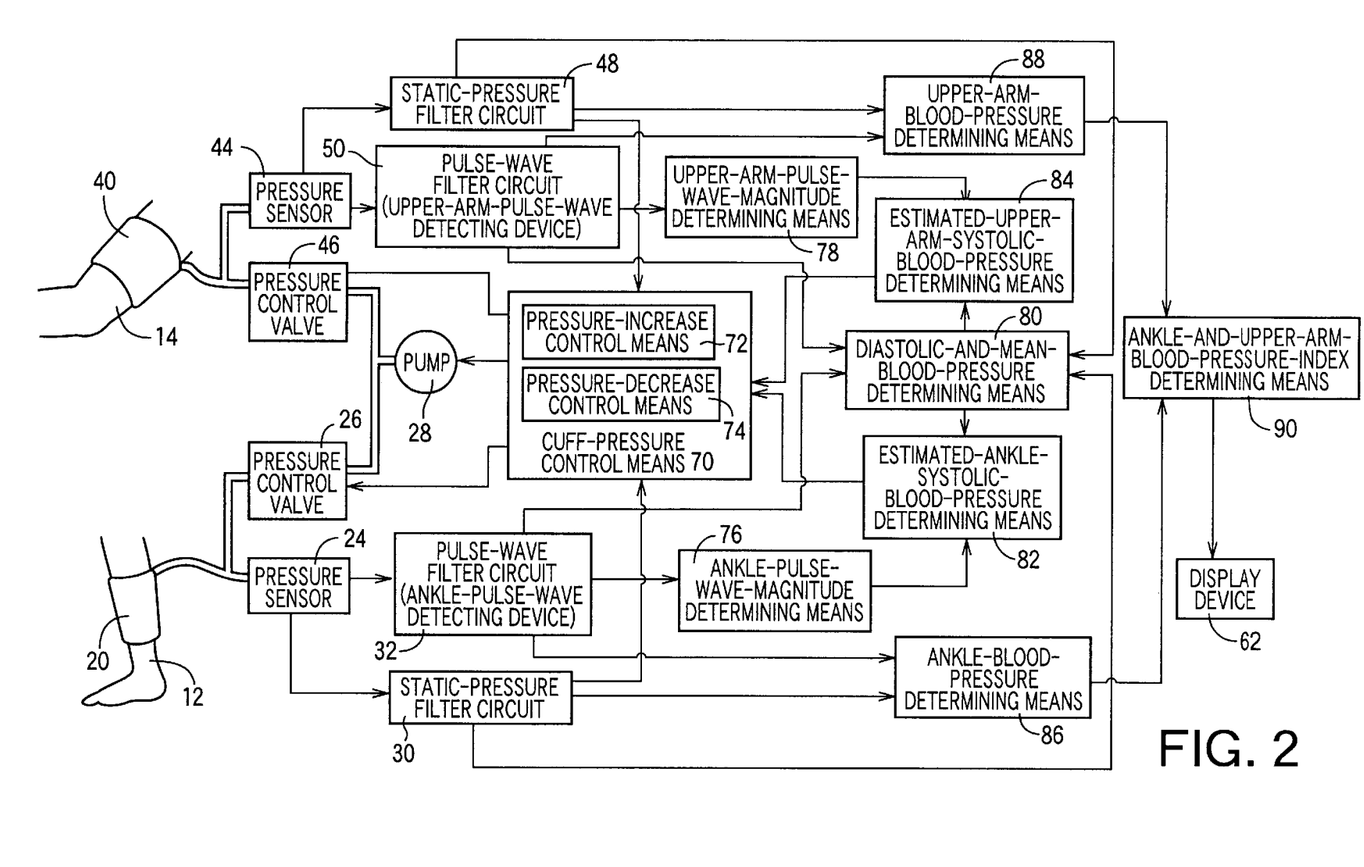
FIG. 2 is a diagrammatic view for explaining essential control functions of an electronic control device of the apparatus of FIG. 1.

FIG. 2 is a diagrammatic view for explaining essential control functions of the electronic control device 36. A cuff-pressure control means 70 includes a pressure-increase control means 72 and a pressure-decrease control means 74. The pressure-increase control means 72 drives the air pump 28 and operates the pressure-control valves 26, 46 so as to increase the ankle cuff pressure $PC_A$ and the upper-arm cuff pressure $PC_B$, from atmospheric pressure to respective pressures higher than respective estimated systolic blood pressures of the ankle 12 and the upper arm 14. More specifically described, the pressure-increase control means 72 controls the ankle cuff pressure $PC_A$, such that first the ankle cuff pressure $PC_A$ is increased to an ankle-pulse-wave detecting pressure $P_A$ pre-set at a pressure estimated to be lower than a diastolic blood pressure $BP(A)_{DIA}$ of the ankle 12, subsequently is kept at the pressure $P_A$ for a time not shorter than a time corresponding to at least one heartbeat of the patient, and then is slowly increased at a pre-set rate (e.g., 3 mmHg/sec). When an estimated-ankle-systolic-blood-pressure determining means 82, described later, determines an estimated ankle systolic blood pressure $EBP(A)_{SYS}$, during the slow increasing of the ankle cuff pressure $PC_A$, the pressure-increase control means 72 increases, at the pre-set rate or a higher rate, the ankle cuff pressure $PC_A$ to a pressure-decrease starting pressure higher by a pre-set pressure $\alpha$ than the estimated ankle systolic blood pressure $EBP(A)_{SYS}$. Similarly, the pressure-increase control means 72 controls the upper-arm cuff pressure $PC_B$, such that first the upper-arm cuff pressure $PC_B$ is increased to an upper-arm-pulse-wave detecting pressure $P_B$ pre-set at a pressure estimated to be lower than a diastolic blood pressure $BP(B)_{DIA}$ of the upper arm 14, subsequently is kept at the pressure $P_B$ for a time not shorter than a time corresponding to at least one heartbeat of the patient, and then is slowly increased at a pre-set rate (e.g., 3 mmHg/sec). When an estimated-upper-arm-systolic-blood-pressure determining means 84, described later, determines an estimated upper-arm systolic blood pressure $EBP(B)_{SYS}$, during the slow increasing of the upper-arm cuff pressure $PC_B$, the pressure-increase control means 72 increases, at the pre-set rate or a higher rate, the upper-arm cuff pressure $PC_B$ to a pressure-decrease starting pressure higher by the pre-set pressure $\alpha$ than the estimated upper-arm systolic blood pressure $EBP(B)_{SYS}$.

The ankle-pulse-wave detecting pressure $P_A$ is pre-set at a pressure which assures that a shape of the ankle pulse wave extracted by the pulse-wave sensor 32 is substantially identical with that of a pressure pulse wave transmitted through an artery underlying the ankle cuff 20; and the upper-arm-pulse-wave detecting pressure $P_B$ is pre-set at a pressure which assures that a shape of the upper-arm pulse wave extracted by the pulse-wave sensor 50 is substantially identical with that of a pressure pulse wave transmitted through an artery underlying the upper-arm cuff 40.

The pressure-decrease control means 74 controls at least one of (a) a timing at which decreasing of at least one of the ankle cuff pressure $PC_A$ and the upper-arm cuff pressure $PC_B$ is started and (b) a rate at which the at least one of the ankle cuff pressure $PC_A$ and the upper-arm cuff pressure $PC_B$ is decreased, so that when the ankle cuff pressure $PC_A$ and the upper-arm cuff pressure $PC_B$ are slowly decreased, the ankle cuff pressure $PC_A$ and the upper-arm cuff pressure $PC_B$ become equal to the estimated ankle systolic blood pressure $EBP(A)_{SYS}$ determined by the estimated-ankle-systolic-blood-pressure determining means 82, and the estimated upper-arm systolic blood pressure $EBP(B)_{SYS}$ determined by the estimated-upper-arm-systolic-blood-pressure determining means 84, respectively, at the same time. The pressure-decrease control means 74 continues the slowly decreasing of the ankle cuff pressure $PC_A$ till an ankle-blood-pressure determining means. 86, described later, determines at least an ankle systolic blood pressure $BP(A)_{SYS}$, and continues the slowly decreasing of the upper-arm cuff pressure $PC_B$ till an upper-arm-blood-pressure determining means 88, described later, determines at least an upper-arm systolic blood pressure $BP(B)_{SYS}$.

Figure 3:
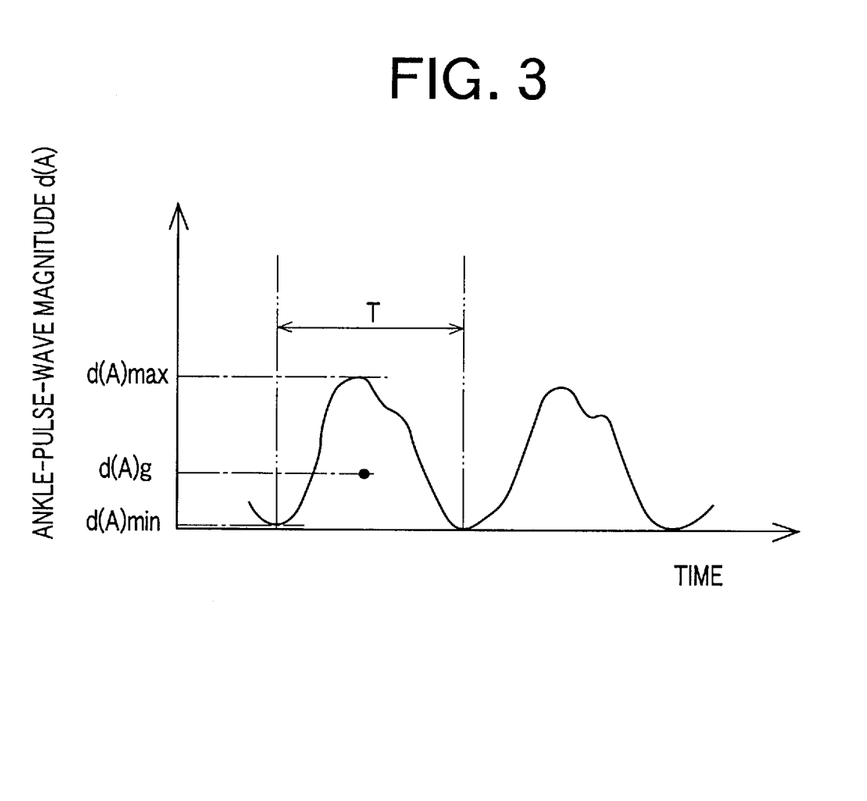
FIG. 3 is a graph showing an example of an ankle pulse wave extracted by a pulse-wave filter circuit of the apparatus of FIG. 1.

An ankle-pulse-wave-magnitude determining means 76 as a sort of inferior-limb-pulse-wave-magnitude determining means determines a minimal magnitude $d(A)min$, an area-gravity-center magnitude $d(A)g$, and a maximal magnitude $d(A)max$ of the ankle pulse wave represented by the ankle-pulse-wave signal $SM_A$ supplied from the pulse-wave filter circuit 32 in a state in which the ankle cuff pressure $PC_A$ is kept at the ankle-pulse-wave detecting pressure $P_A$ by the pressure-increase control means 72. As shown in FIG. 3, the minimal magnitude d(A)min of the ankle pulse wave may be a minimal magnitude of one heartbeat-synchronous pulse d(A) of the ankle pulse wave; the maximal magnitude d(A)max of the ankle pulse wave may be a maximal magnitude of the one heartbeat-synchronous pulse d(A) of the ankle pulse wave; and the area-gravity-center magnitude d(A)g of the ankle pulse wave may be a mean magnitude of the one heartbeat-synchronous pulse d(A) of the ankle pulse wave, i.e., a value obtained by integrating an area defined by the one heartbeat-synchronous pulse d(A) and dividing the integral value by a period T of the one pulse. However, the minimal magnitude d(A)min of the ankle pulse wave may be an average of respective minimal magnitudes of a predetermined number of heartbeat-synchronous pulses d(A) of the ankle pulse wave; the maximal magnitude d(A)max of the ankle pulse wave may be an average of respective maximal magnitudes of the number of heartbeat-synchronous pulses d(A) of the ankle pulse wave; and the area-gravity-center magnitude d(A)g of the ankle pulse wave may be an average of respective mean magnitudes of the number of heartbeat-synchronous pulses d(A) of the ankle pulse wave. Otherwise, the minimal magnitude d(A)min of the ankle pulse wave may be a minimal magnitude of a predetermined number of heartbeat-synchronous pulses d(A) of the ankle pulse wave, or a minimal magnitude of a plurality of heartbeat-synchronous pulses d(A) detected in a predetermined time duration; and the maximal magnitude d(A)max of the ankle pulse wave may be a maximal magnitude of the number of heartbeat-synchronous pulses d(A) of the ankle pulse wave, or a maximal magnitude of a plurality of heartbeat-synchronous pulses d(A) detected in the time duration.

An upper-arm-pulse-wave-magnitude determining means 78 as a sort of superior-limb-pulse-wave-magnitude determining means determines a minimal magnitude d(B)min, an area-gravity-center magnitude d(B)g, and a maximal magnitude d(B)max of the upper-arm pulse wave represented by the upper-arm-pulse-wave signal $SM_B$ supplied from the pulse-wave filter circuit 50 in a state in which the upper-arm cuff pressure $PC_B$ is kept at the upper-arm-pulse-wave detecting pressure $P_B$ by the pressure-increase control means 72. The upper-arm-pulse-wave-magnitude determining means 78 determines the minimal magnitude d(B)min, the area-gravity-center magnitude d(B)g, and the maximal magnitude d(B)max of the upper-arm pulse wave, in a manner identical with the manner in which the ankle-pulse-wave-magnitude determining means 76 determines the minimal magnitude d(A)min, the area-gravity-center magnitude d(A)g, and the maximal magnitude d(A)max of the ankle pulse wave.

A diastolic-and-mean-blood-pressure determining means 80 determines, according to a well-known oscillometric algorithm, an ankle diastolic blood pressure $BP(A)_{DIA}$ and an ankle mean blood pressure $BP(A)_{MEAN}$, based on the ankle pulse wave detected by the pulse-wave filter circuit 32 when the pressure-increase control means 72 slowly increases the ankle cuff pressure $PC_A$, and determines, according to the oscillometric algorithm, an upper-arm diastolic blood pressure $BP(B)_{DIA}$ and an upper-arm mean blood pressure $BP(B)_{MEAN}$, based on the upper-arm pulse wave detected by the pulse-wave filter circuit 50 when the pressure-increase control means 72 slowly increases the upper-arm cuff pressure $PC_B$.

Figure 4:
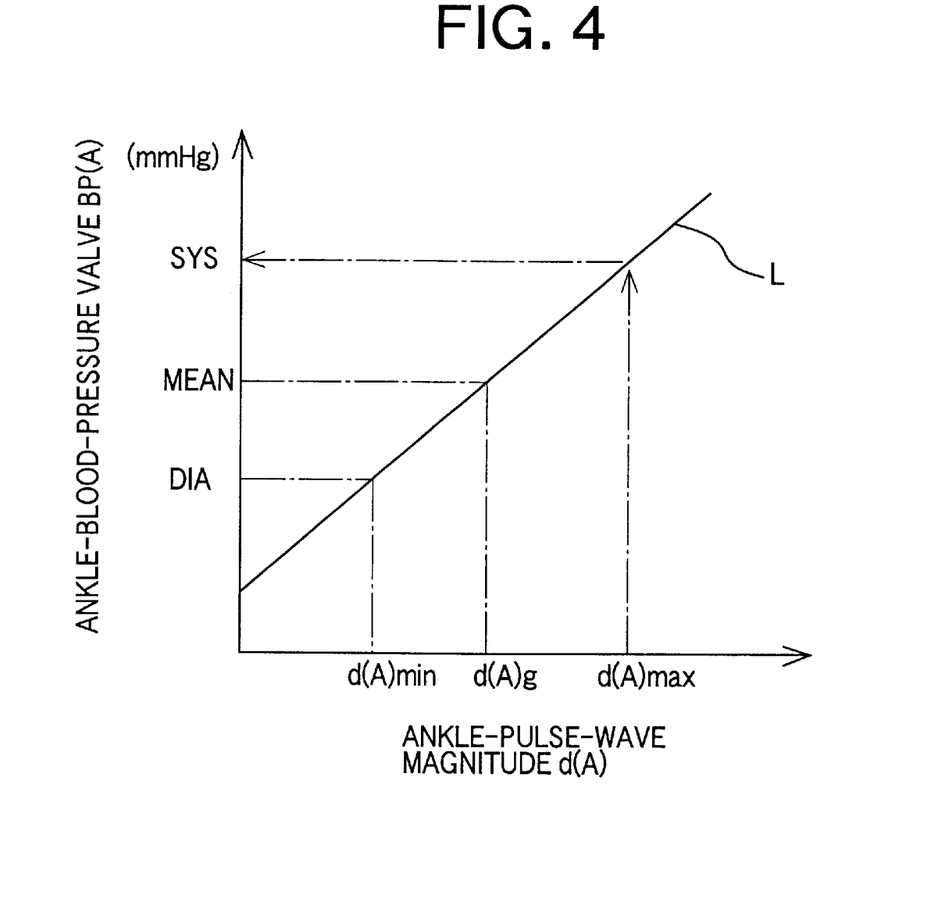
FIG. 4 is a graph showing a relationship, L, between magnitude of ankle pulse wave d(A) and ankle blood pressure BP(A)

The estimated-ankle-systolic-blood-pressure determining means 82 as a sort of estimated-inferior-limb-systolic-blood-pressure determining means determines an estimated systolic blood pressure $EBP(A)_{SYS}$ of the ankle where the ankle cuff 20 is worn, based on the ankle diastolic blood pressure $BP(A)_{DIA}$ and the ankle mean blood pressure $BP(A)_{MEAN}$ determined by the diastolic-and-mean-blood-pressure determining means 80, and the ankle-pulse-wave minimal magnitude d(A)min, the ankle-pulse-wave area-gravity-center magnitude d(A)g, and the ankle-pulse-wave maximal magnitude d(A)max determined by the ankle-pulse-wave-magnitude determining means 76. More specifically described, since the ankle diastolic blood pressure $BP(A)_{DIA}$ corresponds to the minimal magnitude d(A)min of the ankle pulse wave as a pressure pulse wave, and the ankle mean blood pressure $BP(A)_{MEAN}$ corresponds to the area-gravity-center magnitude d(A)g of the ankle pulse wave, a relationship L between ankle-pulse-wave magnitude d(A) and ankle blood pressure value BP(A), as shown in FIG. 4, can be determined based on the ankle diastolic blood pressure $BP(A)_{DIA}$ and the ankle mean blood pressure $BP(A)_{MEAN}$ determined by the diastolic-and-mean-blood-pressure determining means 80, and the ankle-pulse-wave minimal magnitude d(A)min and the ankle-pulse-wave area-gravity-center magnitude d(A)g determined by the ankle-pulse-wave-magnitude determining means 76. And, the estimated ankle systolic blood pressure $EBP(A)_{SYS}$ can be determined, based on the ankle-pulse-wave maximal magnitude d(A)max, according to the thus determined relationship L. However, it is not necessarily required to determine the above-indicated relationship L, because the estimated ankle systolic blood pressure $EBP(A)_{SYS}$ can be determined, based on the ankle-pulse-wave maximal magnitude d(A)max, according to the following Expression 1, Expression 2 derived from Expression 1, or any other proportional expression equivalent to Expression 1:

$$(d(A)\max-d(A)\min):(d(A)g-d(A)\min)=\{EBP(A)_{SYS}-BP(A)_{DIA}\}:\{BP(A)_{MEAN}-BP(A)_{DIA}\} \quad \text{(Expression 1)}$$

$$EBP(A)_{SYS}=\{(d(A)\max-d(A)\min)\times BP(A)_{MEAN}-(d(A)\max-d(A)g)\times BP(A)_{DIA}\}/\{d(A)g-d(A)\min\} \quad \text{(Expression 2)}$$

As the estimated-ankle-systolic-blood-pressure determining means 82 determines the estimated ankle systolic blood pressure $EBP(A)_{SYS}$, the estimated-upper-arm-systolic-blood-pressure determining means 84 as a sort of estimated-superior-limb-systolic-blood-pressure determining means determines an estimated systolic blood pressure $EBP(B)_{SYS}$ of the upper arm where the upper-arm cuff 40 is worn, based on the upper-arm diastolic blood pressure $BP(B)_{DIA}$ and the upper-arm mean blood pressure $BP(B)_{MEAN}$ determined by the diastolic-and-mean-blood-pressure determining means 80, and the upper-arm-pulse-wave minimal magnitude d(B)min, the upper-arm-pulse-wave area-gravity-center magnitude d(B)g, and the upper-arm-pulse-wave maximal magnitude d(B)max determined by the upper-arm-pulse-wave-magnitude determining means 78.

The ankle-blood-pressure determining means 86 determines, according to a well-known oscillometric algorithm, an ankle systolic blood pressure $BP(A)_{SYS}$ based on respective amplitudes of successive heartbeat-synchronous pulses of the ankle pulse wave continuously detected as a heartbeat-synchronous signal during the slow decreasing of the ankle cuff pressure $PC_A$ under the control of the pressure-decrease control means 74. Likewise, the upper-arm-blood-pressure determining means 88 determines, according to the oscillometric algorithm, an upper-arm systolic blood pressure $BP(B)_{SYS}$ based on respective amplitudes of successive heartbeat-synchronous pulses of the upper-arm pulse wave continuously detected as a heartbeat-synchronous signal during the slow decreasing of the upper-arm cuff pressure $PC_B$ under the control of the pressure-decrease control means 74.

An ankle-and-upper-arm blood-pressure-index determining means 90 as a sort of inferior-and-superior-limb blood-pressure-index determining means determines an ABI value, based on the ankle systolic blood pressure $BP(A)_{SYS}$ determined by the ankle-blood-pressure determining means 86 and the upper-arm systolic blood pressure $BP(B)_{SYS}$ determined by the upper-arm-blood-pressure determining means 88, and operates the display device 62 to display the determined ABI value.

Figure 5:
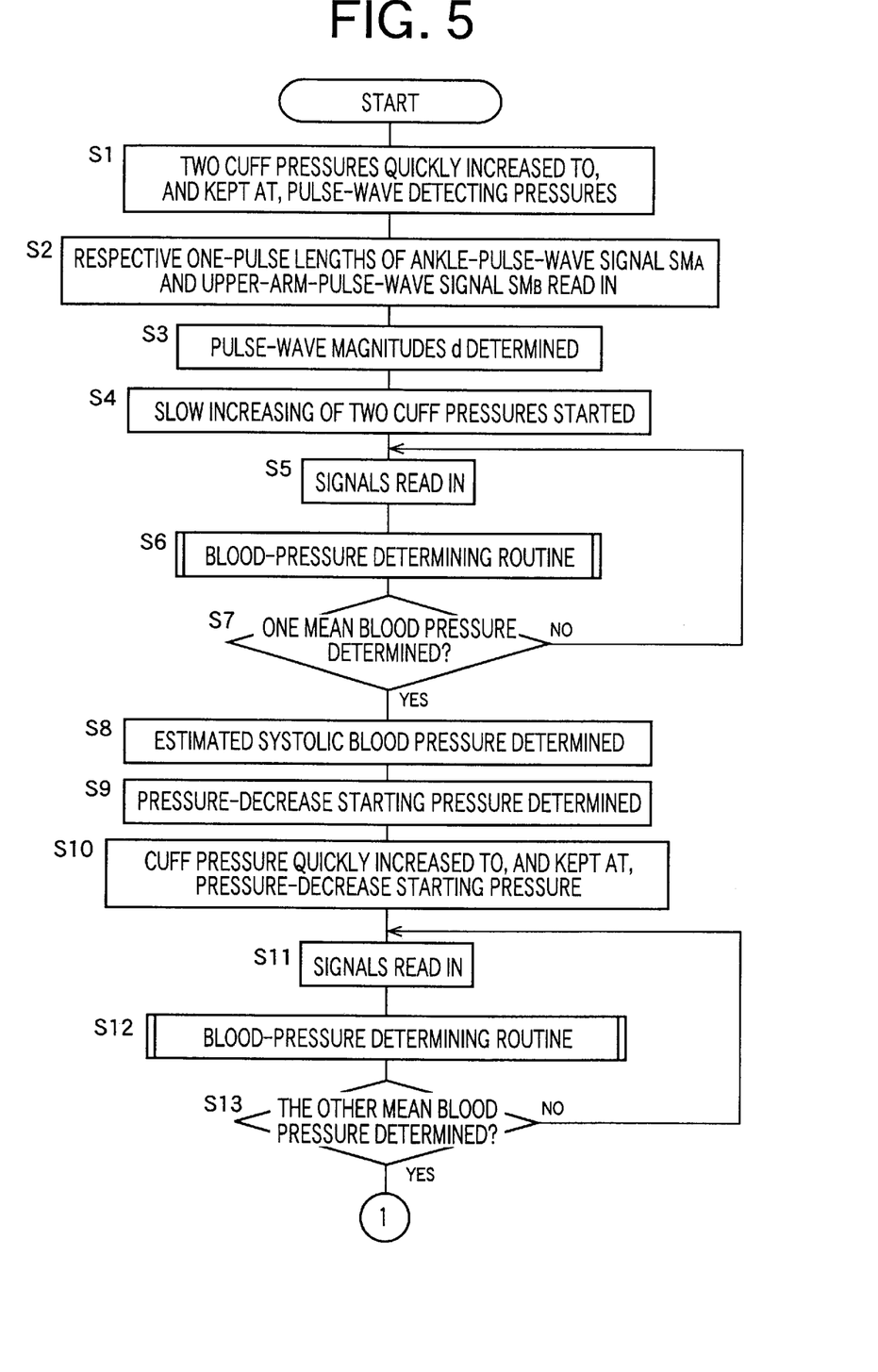
FIG. 5 is a flow chart representing a first portion of a control program that represents the essential control functions of the electronic control device, shown in FIG. 2.
Figure 6:
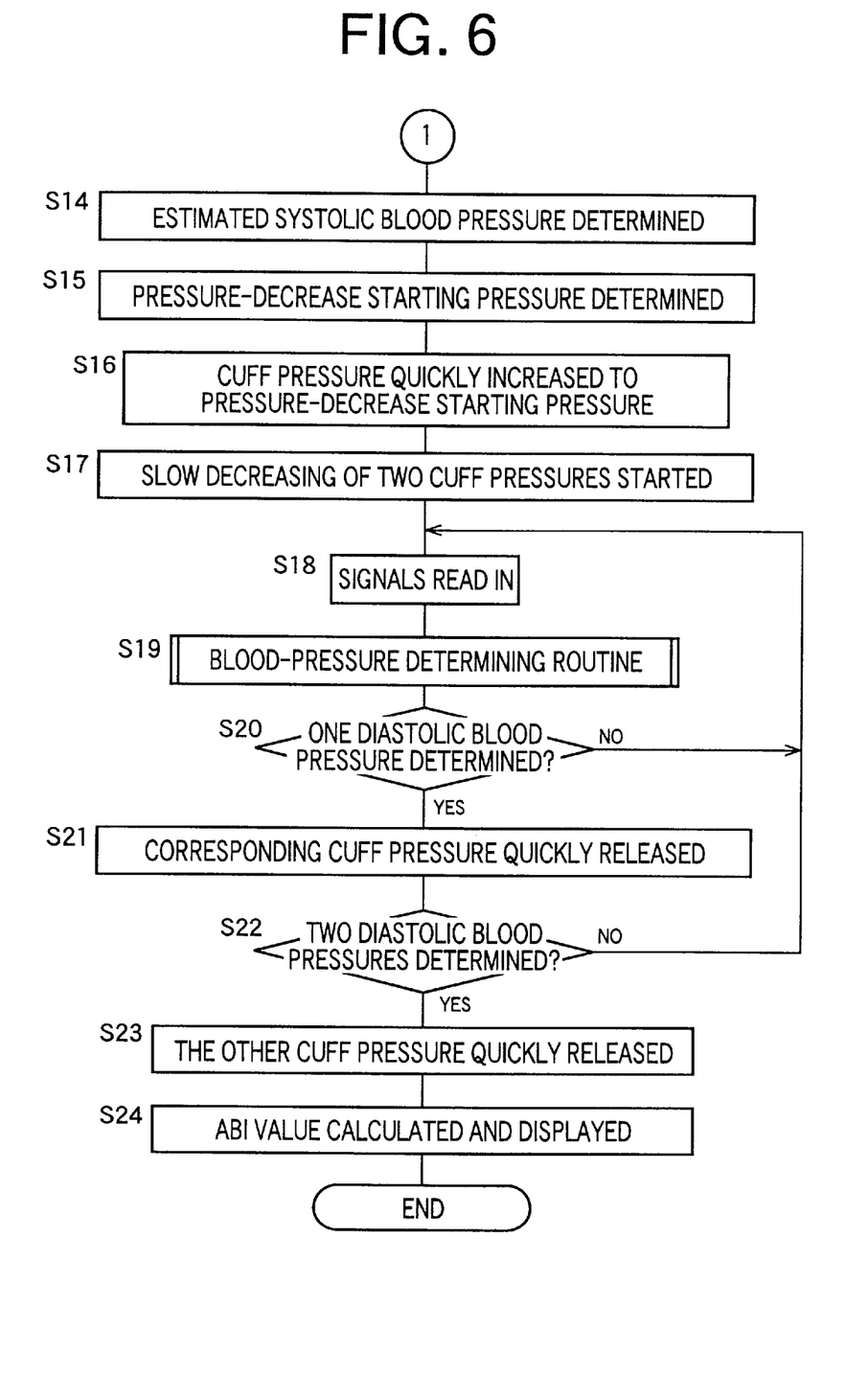
FIG. 6 is a flow chart representing a second portion of the control program that represents the essential control functions of the electronic control device, shown in FIG. 2.
Figure 7:
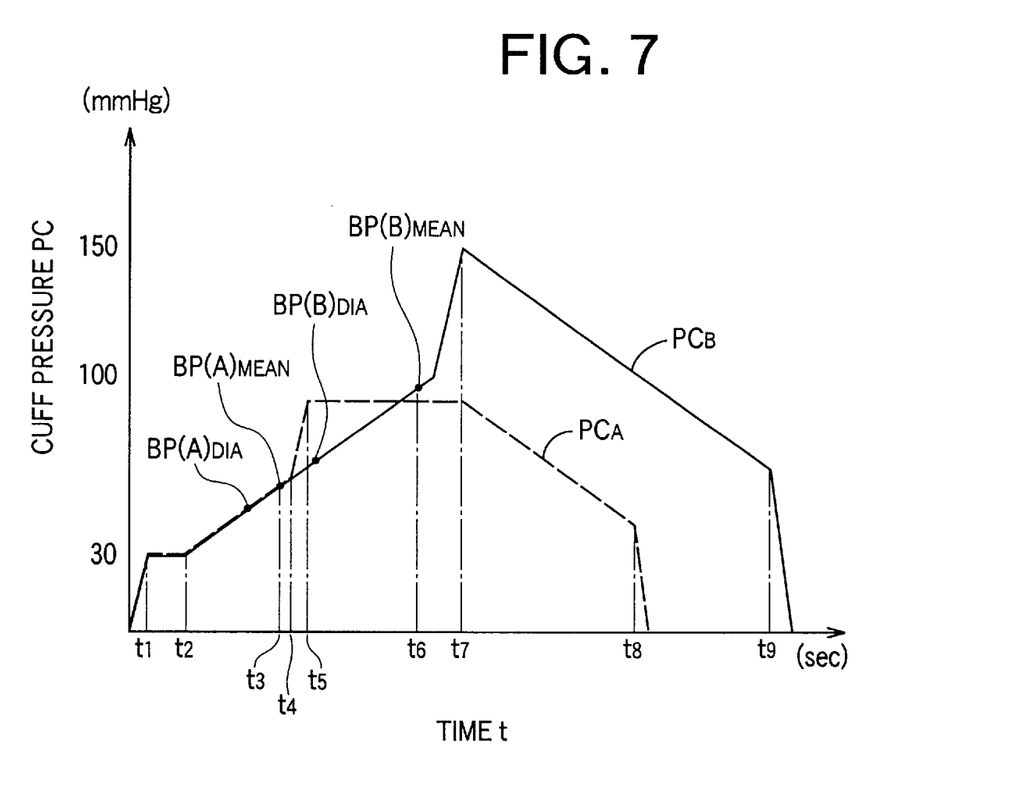
FIG. 7 is a graph showing an example of respective time-wise changes of ankle-cuff pressure $PC_A$ and upper-arm-cuff pressure $PC_B$ that are changed according to the flow charts shown in FIGS. 5 and 6.

FIGS. 5 and 6 are flow charts representing the essential control functions of the electronic control device 36, shown in FIG. 2. FIG. 7 shows a graph representing respective examples of respective time-wise changes of the ankle cuff pressure $PC_A$ and the upper-arm cuff pressure $PC_B$ that are changed according to the flow charts shown in FIGS. 5 and 6. This graph relates to an exemplary case where the upper-arm blood pressure BP(B) is normal but the ankle blood pressure BP(A) is lower than normal blood pressure because the patient has stenosis in the inferior limb including the ankle 12. In FIG. 7, the ankle cuff pressure $PC_A$ is indicated at broken line and the upper-arm cuff pressure $PC_B$ is indicated at solid line.

First, the control device carries out Step S1 (hereinafter, "Step(s)" is omitted) to drive the air pump 28 and operate the pressure control valves 26, 46 so as to start simultaneously increasing the ankle cuff pressure $PC_A$ and the upper-arm cuff pressure $PC_B$, quickly, up to the respective pulse-wave detecting pressures, each pre-set at 30 mmHg, and then keep those pressures thereat (a time point, $t_1$, shown in FIG. 7).

Subsequently, at S2, the control device reads in respective one-heartbeat lengths of the ankle-pulse-wave signal $SM_A$ and the upper-arm-pulse-wave signal $SM_B$, and then the control goes to S3 corresponding to the ankle-pulse-wave-magnitude determining means 76 and the upper-arm-pulse-wave-magnitude determining means 78. At S3, the control device determines a plurality of magnitudes d(A), i.e., a minimal magnitude d(A)min, an area-gravity-center magnitude d(A)g, and a maximal magnitude d(A)max of the ankle pulse wave represented by the ankle-pulse-wave signal $SM_A$ read in at S2, and determines a plurality of magnitudes d(B), i.e., a minimal magnitude d(B)min, an area-gravity-center magnitude d(B)g, and a maximal magnitude d(B)max of the upper-arm pulse wave represented by the upper-arm-pulse-wave signal $SM_B$ read in at S2.

Subsequently, at S4, the control device operates the pressure control valves 26, 46 so as to start slowly increasing the ankle cuff pressure $PC_A$ and the upper-arm cuff pressure $PC_B$, at the respective low rates each pre-set at 3 mmHg/sec (a time point, $t_2$, shown in FIG. 7).

Then, the control device carries out a cyclic loop of S5 to S7. At S5, the control device reads in the ankle-cuff-pressure signal $SC_A$ supplied from the static-pressure filter circuit 30, the ankle-pulse-wave signal $SM_A$ supplied from the pulse-wave filter circuit 32, the upper-arm-cuff-pressure signal $SC_B$ supplied from the static-pressure filter circuit 48, and the upper-arm-pulse-wave signal $SM_B$ supplied from the pulse-wave filter circuit 50; at S6, the control device determines, according to well-known oscillometric blood-pressure-determination algorithm, an ankle diastolic blood pressure $BP(A)_{DIA}$, an ankle mean blood pressure $BP(A)_{MEAN}$, an upper-arm diastolic blood pressure $BP(B)_{DIA}$, and an upper-arm mean blood pressure $BP(B)_{MEAN}$. More specifically described, at S6, the control device determines the ankle diastolic blood pressure $BP(A)_{DIA}$, by first determining respective amplitudes of successive heartbeat-synchronous pulses of the ankle pulse wave represented by the ankle-pulse-wave signal $SM_A$ that are successively read in at S5, then determining a differential curve of the determined amplitudes, and finally determining, as the ankle diastolic blood pressure $BP(A)_{DIA}$, an instantaneous value of the increasing ankle cuff pressure $PC_A$ at a time corresponding to a point of inflection of the differential curve. In addition, at S6, the control device determines the ankle mean blood pressure $BP(A)_{MEAN}$, by first determining an envelope of the respective amplitudes of successive heartbeat-synchronous pulses of the ankle pulse wave, and then determining, as the ankle mean blood pressure $BP(A)_{MEAN}$, an instantaneous value of the increasing ankle cuff pressure $PC_A$ at a time corresponding to a peak point of the envelope, i.e., the greatest amplitude. Likewise, the control device determines the upper-arm diastolic blood pressure $BP(B)_{DIA}$ and the upper-arm mean blood pressure $BP(B)_{MEAN}$.

At S7, the control device judges whether either one of the ankle mean blood pressure $BP(A)_{MEAN}$ and the upper-arm mean blood pressure $BP(A)_{MEAN}$ has been determined. The result of this judgment depends on whether the patient has arteriostenosis or not, or what degree of arteriosclerosis the patient has. In the exemplary case where the patient has arteriostenosis in the inferior limb but does not have it in the superior limb, the ankle mean blood pressure $BP(A)_{MEAN}$ is determined at a time point, $t_3$, shown in FIG. 7. When the ankle blood pressure values BP(A) are determined during the slow increasing of the ankle cuff pressure $PC_A$, the diastolic ankle blood pressure $BP(A)_{DIA}$ is determined prior to the determination of the ankle mean blood pressure $BP(A)_{MEAN}$, as shown in FIG. 7.

If a negative judgment is made at S7, the control device repeats S5 and the following steps. Meanwhile, if a positive judgment is made at S7, the control proceeds with S8 corresponding to the estimated-ankle-systolic-blood-pressure determining means 82 or the estimated-upper-arm-systolic-blood-pressure determining means 84. At S8, the control device determines an estimated systolic blood pressure $EBP_{SYS}$ of one of the ankle 12 and the upper arm 14 that corresponds to the one mean blood pressure $BP_{MEAN}$ the determination of which has been judged at S7. Regarding the example shown in FIG. 7, the control device determines an estimated ankle systolic blood pressure $EBP(A)_{SYS}$, by substituting the ankle-pulse-wave minimal magnitude d(A)min, the ankle-pulse-wave area-gravity-center magnitude d(A) min, and the ankle-pulse-wave maximal magnitude d(A) max, each determined at S3, and the ankle diastolic blood pressure $BP(A)_{DIA}$ and the ankle mean blood pressure $BP(A)_{MEAN}$, each determined at S6, for the above-indicated Expression 2.

Then, at S9, the control device adds a pre-set pressure value α (e.g., 20 mmHg) to the estimated ankle systolic blood pressure $EBP(A)_{SYS}$ determined at S8, and adopts the thus obtained pressure as a pressure-decrease starting pressure from which the ankle cuff pressure $PC_A$ is to be decreased. Subsequently, at S10, the control device operates the pressure control valve 26 to increase quickly the ankle cuff pressure $PC_A$, at a high rate (e.g., 6 mmHg/sec), to the pressure-decrease starting pressure determined at S9 (a time point, $t_4$, shown in FIG. 7), and then keeps the ankle cuff pressure $PC_A$ thereat (a time point, $t_5$, shown in FIG. 7).

Subsequently, the control device carries out a cyclic loop of S11 to S13. S11 and S12 are identical with S5 and S6. That is, at S11, the control device reads in the ankle-cuff-pressure signal $SC_A$, the ankle-pulse-wave signal $SM_A$, the upper-arm-cuff-pressure signal $SC_B$, and the upper-armpulse-wave signal $SM_B$; and at S12, the control device carries out the oscillometric blood-pressure-determination algorithm. At S13, the control device judges whether the other mean blood pressure $BP_{MEAN}$ that had not been determined in the cyclic loop of S5 to S7, has been determined. Regarding the example shown in FIG. 7, the control device judges whether the upper-arm mean blood pressure $BP(B)_{MEAN}$ has been determined.

If a negative judgment is made at S13, the control device repeats S11 and the following steps. In the flow charts shown in FIGS. 5 and 6, S6 and S12 correspond to the diastolic-and-mean-blood-pressure determining means 80. Although a negative judgment is made at S13 during an initial period, a positive judgment is made at a time point, $t_6$, shown in FIG. 7. The upper-arm diastolic blood pressure $BP(B)_{DIA}$ has been already determined at the time point $t_6$.

Meanwhile, if a positive judgment is made at S7, then the control proceeds with S14 corresponding to the estimated-ankle-systolic-blood-pressure determining means 82 or the estimated-upper-arm-systolic-blood-pressure determining means 84. At S14, the control device determines an estimated systolic blood pressure $EBP_{SYS}$ of the other of the ankle 12 and the upper arm 14 that corresponds to the other mean blood pressure $BP_{MEAN}$ the determination of which has been judged at S13. Regarding the example shown in FIG. 7, the control device determines an estimated upper-arm systolic blood pressure $EBP(B)_{SYS}$, by substituting the upper-arm-pulse-wave minimal magnitude d(B)min, the upper-arm-pulse-wave area-gravity-center magnitude d(B) min, and the upper-arm-pulse-wave maximal magnitude d(B)max, each determined at S3, and the upper-arm diastolic blood pressure $BP(B)_{DIA}$ and the upper-arm mean blood pressure $BP(B)_{MEAN}$, each determined at S12, for the following Expression 3 that is obtained by replacing, in Expression 2, the ankle pulse-wave magnitudes d(A) and the ankle blood-pressure values BP(A) with the upper-arm pulse-wave magnitudes d(B) and the upper-arm blood-pressure values BP(B):

$$EBP(B)_{SYS} = \{(d(B)max - d(B)min) \times BP(B)_{MEAN} - (d(B)_{max} - d(B)g) \times BP(B)_{DIA}\} / \{d(B)g - d(B)min\} \quad \text{(Expression 3)}$$

Then, at S15, the control device adds the pre-set pressure value α (e.g., 20 mmHg) to t he estimated upper-arm systolic blood pressure $EBP(B)_{SYS}$ determined at S14, and adopts the thus obtained pressure as a pressure-decrease starting pressure from which the upper-arm cuff pressure $PC_B$ is to be decreased. Subsequently, at S16, the control device operates the pressure control valve 46 to increase quickly the upper-arm cuff pressure $PC_B$, at a high rate (e.g., 6 mmHg/sec), to the pressure-decrease starting pressure determined at S15. In the flow charts shown in FIGS. 5 and 6, S1, S4, S9, S10, S15, and S16 correspond to the pressure-increase control means 72.

Subsequently, at S17, the control device stops the air pump 28 and operates the pressure control valves 26, 46 so as to simultaneously start decreasing the two cuff pressures $PC_A$, $PC_B$, at the low rate of 3 mmHg/sec, from the respective pressure-decrease starting pressures (a time point, $t_7$, shown in FIG. 7). Since the estimated ankle systolic blood pressure $EBP(A)_{SYS}$ and the estimated upper-arm systolic blood pressure $EBP(B)_{SYS}$ are determined during the slow increasing of the respective cuff pressures $PC_A$, $PC_B$, and the common pressure value α is added to each of the two estimated blood pressures $EBP(A)_{SYS}$, $EBP(B)_{SYS}$ to determine the respective pressure-decrease starting pressures from which the two cuff pressures $PC_A$, $PC_B$ are to be decreased, and since the decreasing of the two cuff pressures $PC_A$, $PC_B$ are simultaneously started, and the two cuff pressures $PC_A$, $PC_B$ are decreased at the common rate, the two cuff pressures $PC_A$, $PC_B$ become equal to the respective estimated blood pressures $EBP(A)_{SYS}$, $EBP(B)_{SYS}$ at the same time.

Then, the control device carries out a cyclic loop of S18 to S22. S18 and S19 are identical with S5 and S6. That is, at S18, the control device reads in the ankle-cuff-pressure signal $SC_A$, the ankle-pulse-wave signal $SM_A$, the upper-arm-cuff-pressure signal $SC_B$, and the upper-arm-pulse-wave signal $SM_B$; and at S19 corresponding to the ankle-blood-pressure determining means 86 and the upper-arm-blood-pressure determining means 88, the control device carries out the oscillometric blood-pressure-determination algorithm. At S20, the control device judges whether either one of the ankle diastolic blood pressure $BP(A)_{DIA}$ and the upper-arm diastolic blood pressure $BP(B)_{DIA}$ has been determined. If a negative judgment is made at S20, the control device repeats S18 and the following steps. While the control device iteratively carries out a cyclic loop of S18 to S20, the control device determines an ankle systolic blood pressure $BP(A)_{SYS}$ and an upper-arm systolic blood pressure $BP(B)_{SYS}$, at substantially the same time, because, during the decreasing of the ankle and upper-arm cuff pressures $PC_A$, $PC_B$, the two cuff pressures $PC_A$, $PC_B$ become equal to the respective estimated blood pressures $EBP(A)_{SYS}$, $EBP(B)_{SYS}$ at the same time.

On the other hand, if a positive judgment is made at S20, the control goes to S21 to operate one of the two pressure control valves 26, 46 that corresponds to the one diastolic blood pressure $BP_{DIA}$ the determination of which has been judged at S20, and thereby quickly release the pressure of one of the two cuffs 26, 46 that corresponds to the one pressure control valve. Regarding the example shown in FIG. 7, since the ankle diastolic blood pressure $BP(A)_{DIA}$ is determined earlier, the control device operates, at S21, the pressure control valve 26 to quickly release the ankle cuff pressure $PC_A$ (a time point, $t_8$, shown in FIG. 7).

At S22, the control device judges whether both of the ankle diastolic blood pressure $BP(A)_{DIA}$ and the upper-arm diastolic blood pressure $BP(B)_{DIA}$ have been determined. If a negative judgment is made at S22, the control device repeats S18 and the following steps, so as to determine the other of the two diastolic blood pressures, e.g., the upper-arm diastolic blood pressure $BP(B)_{DIA}$. Meanwhile, if a positive judgment is made at S22, the control goes to S23 to quickly release the other cuff pressure, e.g., the upper-arm cuff pressure $PC_B$ (a time point, $t_9$, shown in FIG. 7). In the flow charts shown in FIGS. 5 and 6, S17, S21, and S23 correspond to the pressure-decrease control means 74.

Then, the control proceeds with S24 corresponding to the ankle-and-upper-arm blood-pressure-index determining means 90. At S24, the control device determines an ABI value by dividing the ankle systolic blood pressure $BP(A)_{SYS}$ determined in the cyclic loop of S18 to S20, by the upper-arm systolic blood pressure $BP(B)_{SYS}$ determined in the same loop, and operates the display device 62 to display the thus determined ABI value.

In the embodiment employing the flow charts shown in FIGS. 5 and 6, at S8 (the estimated-ankle-systolic-blood-pressure determining means 82), the control device determines, during the increasing of the ankle cuff pressure $PC_A$, the estimated ankle systolic blood pressure $EBP(A)_{SYS}$; and, at S14 (the estimated-upper-arm-systolic-blood-pressure determining means 84), the control device determines, during the increasing of the upper-arm cuff pressure $PC_B$, the estimated upper-arm systolic blood pressure EBP(B)$_{SYS}$. Subsequently, at S9, S10, and S15 to S17 (the cuff-pressure control means 70), the control device controls, during the decreasing of the ankle cuff pressure PC$_A$ and the upper-arm cuff pressure PC$_B$, the two cuff pressures PC$_A$, PC$_B$, such that the two cuff pressures PC$_A$, PC$_B$ become equal to the respective estimated systolic blood pressures EBP(A)$_{SYS}$, EBP(B)$_{SYS}$, at the same time. Thus, in the single blood-pressure measuring operation, the present apparatus can measure the ankle systolic blood pressure BP(A)$_{SYS}$ and the upper-arm systolic blood pressure BP(A)$_{SYS}$, at substantially the same time.

In the embodiment employing the flow charts shown in FIGS. 5 and 6, while the cuff pressures PC$_A$, PC$_B$ are increased at S1 and S4 (the pressure-increase control means 72), the control device reads in, at S2, the ankle pulse wave extracted by the pulse-wave filter circuit 32 and the upper-arm pulse wave extracted by the upper-arm filter circuit 50, and determines, at S6 and S12 (the diastolic-and-mean-blood-pressure determining means 80), the ankle diastolic blood pressure BP(A)$_{DIA}$, the ankle mean blood pressure BP(A)$_{MEAN}$, the upper-arm diastolic blood pressure BP(B)$_{DIA}$, and the upper-arm mean blood pressure BP(B)$_{MEAN}$. And, at S8 (the estimated-ankle-systolic-blood-pressure determining means 82), the control device determines the estimated ankle systolic blood pressure EBP(A)$_{SYS}$ based on the ankle diastolic blood pressure BP(A)$_{DIA}$ and the ankle mean blood pressure BP(A)$_{MEAN}$, each actually measured, and the ankle-pulse-wave minimal magnitude d(A)min, the ankle-pulse-wave area-gravity-center magnitude d(A)g, and the ankle-pulse-wave maximal magnitude d(A)max, each actually detected; and, at S14 (the estimated-upper-arm-systolic-blood-pressure determining means 84), the control device determines the estimated upper-arm systolic blood pressure EBP(B)$_{SYS}$ based on the upper-arm diastolic blood pressure BP(B)$_{DIA}$ and the upper-arm mean blood pressure BP(A)$_{MEAN}$, each actually measured, and the upper-arm-pulse-wave minimal magnitude d(B)min, the upper-arm-pulse-wave area-gravity-center magnitude d(B)g, and the upper-arm-pulse-wave maximal magnitude d(B)max, each actually detected. Thus, the present apparatus can determine, with high accuracy, the estimated ankle systolic blood pressure EBP(A)$_{SYS}$ and the estimated upper-arm systolic blood pressure EBP(B)$_{SYS}$, and accordingly can measure, in the single blood-pressure measuring operation, the ankle systolic blood pressure BP(A)$_{SYS}$ and the upper-arm systolic blood pressure BP(A)$_{SYS}$, at the same time, with high accuracy.

In the embodiment employing the flow charts shown in FIGS. 5 and 6, while the ankle cuff pressure PC$_A$ and the upper-arm cuff pressure PC$_B$ are slowly increased at S4 (the pressure-increase control means 72), the control device determines, at S6 and S12 (the diastolic-and-mean-blood-pressure determining means 80), the ankle mean blood pressure BP(A)$_{MEAN}$ and the upper-arm mean blood pressure BP(B)$_{MEAN}$. And, at S8 (the estimated-ankle-systolic-blood-pressure determining means 82) and at S14 (the estimated-upper-arm-systolic-blood-pressure determining means 84), the control device determines the estimated ankle systolic blood pressure EBP(A)$_{SYS}$ based on the ankle pulse wave obtained before the determination of the ankle mean blood pressure BP(A)$_{MEAN}$, and determines the estimated upper-arm systolic blood pressure EBP(B)$_{SYS}$ based on the upper-arm pulse wave obtained before the determination of the upper-arm mean blood pressure BP(B)$_{MEAN}$. Then, at S16 (the pressure-increase control means 72), the control device quickly increases the cuff pressure corresponding to one mean blood pressure determined later than the other mean blood pressure, e.g., the upper-arm cuff pressure PC$_B$, to the pressure-decrease starting pressure determined based on, e.g., the estimated upper-arm systolic blood pressure EBP(B)$_{SYS}$. Thus, the control device can increase the ankle cuff pressure PC$_A$ and the upper-arm cuff pressure PC$_B$ to the respective pressure-decrease starting pressures, in a shorter time than a time in which the two cuff pressures are slowly increased till an ankle systolic blood pressure BP(A)$_{SYS}$ and an upper-arm systolic blood pressure BP(B)$_{SYS}$ are measured so that the measured ankle and upper-arm systolic blood pressures BP(A)$_{SYS}$, BP(B)$_{SYS}$ are used as estimated ankle and upper-arm systolic blood pressures EBP(A)$_{SYS}$, EBP(B)$_{SYS}$.

While the present invention has been described in its embodiment by reference to the drawings, it is to be understood that the invention may otherwise be embodied.

For example, according to the flow charts shown in FIGS. 5 and 6, the cuff pressure corresponding to one pressure-decrease starting pressure determined earlier than the other pressure-decrease starting pressure, is increased, at the high rate (at S10), up to the one starting pressure after the determination of the one starting pressure. However, it is possible to keep the low rate so that the cuff pressure is increased at the low rate up to the one starting pressure.

In the illustrated ankle-and-upper-arm blood-pressure-index measuring apparatus 10, the estimated ankle systolic blood pressure EBP(A)$_{SYS}$ is determined based on the ankle diastolic and mean blood pressure values BP(A)$_{DIA}$, BP(A)$_{MEAN}$ each determined during the slow increasing of the ankle cuff pressure PC$_A$. However, during the slow increasing of the ankle cuff pressure PC$_A$, it is possible to determine an ankle systolic blood pressure BP(A)$_{SYS}$ and adopt the thus determined systolic blood pressure BP(A)$_{SYS}$ as an estimated ankle systolic blood pressure EBP(A)$_{SYS}$. Similarly, during the slow increasing of the upper-arm cuff pressure PC$_B$, it is possible to determine an upper-arm systolic blood pressure BP(B)$_{SYS}$ and adopt the thus determined systolic blood pressure BP(B)$_{SYS}$ as an estimated upper-arm systolic blood pressure EBP(B)$_{SYS}$.

In the above-described case where, during the slow increasing of the cuff pressure PC, the systolic blood pressure BP$_{SYS}$ is determined and the thus determined systolic blood pressure BP$_{SYS}$ is adopted as the estimated systolic blood pressure EBP$_{SYS}$, it is not needed to determine the mean blood pressure BP$_{MEAN}$. Therefore, the ankle-blood-pressure measuring device 16 and the upper-arm-blood-pressure measuring device 18 may be of so-called K-sound type wherein systolic and diastolic blood pressure values are determined based on respective instantaneous values of the cuff pressure at respective times when Korotkoff sounds are first and last detected. Otherwise, those devices 16, 18 may be of ultrasonic-Doppler-effect type wherein ultrasonic-wave transmitter and receiver, placed right above an artery, cooperate with each other to detect opening and closing of the artery during changing of a pressing pressure applied to the artery.

The above-described ankle-pulse-wave-magnitude determining means 76 determines the magnitudes d(A) of the ankle pulse wave detected in the state in which the ankle cuff pressure PC$_A$ is kept at the ankle-pulse-wave detecting pressure P$_A$ by the pressure-increase control means 72. However, the determining means 76 may be adapted to determine magnitudes d(A) of an ankle pulse wave detected during increasing of the ankle cuff pressure PC$_A$. Likewise, the upper-arm-pulse-wave-magnitude determining means 78 may be adapted to determine magnitudes d(B) of an upper-arm pulse wave detected during increasing of the upper-arm cuff pressure PC$_B$.

It is to be understood that the present invention may be embodied with other changes, improvements and modifications that may occur to a person skilled in the art without departing from the spirit and scope of the invention defined in the appended claims.

What is claimed is:

1. An apparatus for measuring an inferior-and-superior-limb blood-pressure index of a living subject, comprising:

an inferior-limb blood-pressure measuring device which includes an inferior-limb cuff adapted to be wound around a portion of an inferior limb of the subject and measures a systolic blood pressure of the inferior limb based on a heartbeat-synchronous signal which is obtained from the subject when a pressure of the inferior-limb cuff is decreased after the pressure of the inferior-limb cuff is increased up to a pressure higher than an estimated systolic blood pressure of the portion of the inferior limb;

a superior-limb blood-pressure measuring device which includes a superior-limb cuff adapted to be wound around a portion of a superior limb of the subject and measures a systolic blood pressure of the superior limb based on a heartbeat-synchronous signal which is obtained from the subject when a pressure of the superior-limb cuff is decreased after the pressure of the superior-limb cuff is increased up to a pressure higher than an estimated systolic blood pressure of the portion of the superior limb;

an inferior-and-superior-limb-blood-pressure-index determining means for determining the inferior-and-superior-limb blood-pressure index of the subject, based on the systolic blood pressure of the inferior limb measured by the inferior-limb blood-pressure measuring device and the systolic blood pressure of the superior limb measured by the superior-limb blood-pressure measuring device;

an estimated-inferior-limb-systolic-blood-pressure determining means for determining the estimated systolic blood pressure of the portion of the inferior limb based on a heartbeat-synchronous signal which is obtained from the subject when the pressure of the inferior-limb cuff is increased;

an estimated-superior-limb-systolic-blood-pressure determining means for determining the estimated systolic blood pressure of the portion of the superior limb based on a heartbeat-synchronous signal which is obtained from the subject when the pressure of the superior-limb cuff is increased; and a cuff-pressure control means for controlling at least one of the respective pressures of the inferior-limb cuff and the superior-limb cuff, such that when the respective pressures of the inferior-limb cuff and the superior-limb cuff are decreased, the respective pressures of the inferior-limb cuff and the superior-limb cuff become equal to the respective estimated systolic blood pressures of the inferior limb and the superior limb, at a same time.

2. An apparatus according to claim 1, wherein the cuff-pressure control means comprises a pressure-increase control means for increasing the pressure of the inferior-limb cuff from a pressure which is estimated to be lower than a diastolic blood pressure of the portion of the inferior limb, and increasing the pressure of the superior-limb cuff from a pressure which is estimated to be lower than a diastolic blood pressure of the portion of the superior limb, wherein the apparatus further comprises:

a diastolic-and-mean-blood-pressure measuring device which measures a diastolic-blood pressure and a mean blood pressure of the inferior limb based on the heartbeat-synchronous signal obtained from the subject when the pressure of the inferior-limb cuff is increased by the pressure-increase control means, and measures a diastolic blood pressure and a mean blood pressure of the superior limb based on the heartbeat-synchronous signal obtained from the subject when the pressure of the superior-limb cuff is increased by the pressure-increase control means;

an inferior-limb-pulse-wave detecting device which detects an inferior-limb pulse wave that is an oscillation of the pressure of the inferior-limb cuff;

a superior-limb-pulse-wave detecting device which detects a superior-limb pulse wave that is an oscillation of the pressure of the superior-limb cuff;

an inferior-limb-pulse-wave-magnitude determining means for determining a minimal magnitude, an area-gravity-center magnitude, and a maximal magnitude of at least one heartbeat-synchronous pulse of the inferior-limb pulse wave detected by the inferior-limb-pulse-wave detecting device in a state in which the pressure of the inferior-limb cuff is kept at a pressure which is estimated to be lower than a mean blood pressure of the portion of the inferior limb; and a superior-limb-pulse-wave-magnitude determining means for determining a minimal magnitude, an area-gravity-center magnitude, and a maximal magnitude of at least one heartbeat-synchronous pulse of the superior-limb pulse wave detected by the superior-limb-pulse-wave detecting device in a state in which the pressure of the superior-limb cuff is kept at a pressure which is estimated to be lower than a mean blood pressure of the portion of the superior limb, and wherein the estimated-inferior-limb-systolic-blood-pressure determining means determines the estimated systolic blood pressure of the portion of the inferior limb based on the diastolic blood pressure and the mean blood pressure of the inferior limb, measured by the systolic-and-mean-blood-pressure measuring device, and the minimal magnitude, the area-gravity-center magnitude, and the maximal magnitude of the inferior-limb pulse wave, determined by the inferior-limb-pulse-wave-magnitude determining means, and the estimated-superior-limb-systolic-blood-pressure determining means determines the estimated systolic blood pressure of the portion of the superior limb based on the diastolic blood pressure and the mean blood pressure of the superior limb, measured by the systolic-and-mean-blood-pressure measuring device, and the minimal magnitude, the area-gravity-center magnitude, and the maximal magnitude of the superior-limb pulse wave, determined by the superior-limb-pulse-wave-magnitude determining means.

3. An apparatus according to claim 2, wherein the estimated-inferior-limb-systolic-blood-pressure determining means comprises:

means for determining a first linear relationship between blood pressure and pulse-wave magnitude, based on the diastolic blood pressure and the mean blood pressure of the inferior limb, and the minimal magnitude and the area-gravity-center magnitude of the inferior-limb pulse wave; and means for determining, according to the first linear relationship between blood pressure and pulse-wave magnitude, the estimated systolic blood pressure of the portion of the inferior limb, based on the maximal magnitude of the inferior-limb pulse wave, and wherein the estimated-superior-limb-systolic-blood-pressure determining means comprises:

means for determining a second linear relationship between blood pressure and pulse-wave magnitude, based on the diastolic blood pressure and the mean blood pressure of the superior limb, and the minimal magnitude and the area-gravity-center magnitude of the superior-limb pulse wave; and means for determining, according to the second linear relationship between blood pressure and pulse-wave magnitude, the estimated systolic blood pressure of the portion of the superior limb, based on the maximal magnitude of the superior-limb pulse wave.

4. An apparatus according to claim 2, wherein the inferior-limb-pulse-wave-magnitude determining means determines the area-gravity-center magnitude of the heartbeat-synchronous pulse of the inferior-limb pulse wave, by determining a first area defined by the heartbeat-synchronous pulse and dividing the determined first area by a period of the heartbeat-synchronous pulse of the inferior-limb pulse wave, and the superior-limb-pulse-wave-magnitude determining means determines the area-gravity-center magnitude of the heartbeat-synchronous pulse of the superior-limb pulse wave, by determining a second area defined by the heartbeat-synchronous pulse of the superior-limb pulse wave and dividing the determined second area by a period of the heartbeat-synchronous pulse of the superior-limb pulse wave.

5. An apparatus according to claim 1, further comprising a mean-blood-pressure measuring device which measures a mean blood pressure of the inferior limb based on the heartbeat-synchronous signal obtained from the subject when the pressure of the inferior-limb cuff is increased, and measures a mean blood pressure of the superior limb based on the heartbeat-synchronous signal obtained from the subject when the pressure of the superior-limb cuff is increased, wherein the estimated-inferior-limb-systolic-blood-pressure determining means determines the estimated systolic blood pressure of the portion of the inferior limb based on the heartbeat-synchronous signal obtained from the subject when the pressure of the inferior-limb cuff is increased and before the mean blood pressure of the inferior limb is measured by the mean-blood-pressure measuring device, wherein the estimated-superior-limb-systolic-blood-pressure determining means determines the estimated systolic blood pressure of the portion of the superior limb based on the heartbeat-synchronous signal obtained from the subject when the pressure of the superior-limb cuff is increased and before the mean blood pressure of the superior limb is measured by the mean-blood-pressure measuring device, and wherein the cuff-pressure control means comprises a pressure-increase control means for increasing, at a first rate, the pressure of the inferior-limb cuff from a pressure which is estimated to be lower than a diastolic blood pressure of the portion of the inferior limb, and increasing, at a second rate, the pressure of the superior-limb cuff from a pressure which is estimated to be lower than a diastolic blood pressure of the portion of the superior limb, and further increasing, at a third rate higher than the first rate, the pressure of the inferior-limb cuff to a first pressure-decrease starting pressure determined based on the estimated systolic blood pressure of the inferior limb determined by the estimated-inferior-limb-systolic-blood-pressure determining means, when the mean blood pressure of the inferior limb is measured by the mean-blood-pressure measuring device, at a time later than a time when the mean blood pressure of the superior limb is measured by the mean-blood-pressure measuring device, and further increasing, at a fourth rate higher than the second rate, the pressure of the superior-limb cuff to a second pressure-decrease starting pressure determined based on the estimated systolic blood pressure of the superior limb determined by the estimated-superior-limb-systolic-blood-pressure determining means, when the mean blood pressure of the superior limb is measured at a time later than a time when the mean blood pressure of the inferior limb is measured.

6. An apparatus according to claim 5, wherein the cuff-pressure control means comprises:

means for determining, as the first pressure-decrease starting pressure from which the pressure of the inferior-limb cuff is to be decreased, a pressure higher by a first prescribed pressure than the estimated systolic blood pressure of the inferior limb determined by the estimated-inferior-limb-systolic-blood-pressure determining means; and means for determining, as the second pressure-decrease starting pressure from which the pressure of the superior-limb cuff is to be decreased, a pressure higher by a second prescribed pressure than the estimated systolic blood pressure of the superior limb determined by the estimated-superior-limb-systolic-blood-pressure determining means.

7. An apparatus according to claim 1, wherein the cuff-pressure control means comprises:

means for determining, as a first pressure-decrease starting pressure from which the pressure of the inferior-limb cuff is to be to decreased, a pressure higher by a prescribed pressure than the estimated systolic blood pressure of the inferior limb determined by the estimated-inferior-limb-systolic-blood-pressure determining means;

means for determining, as a second pressure-decrease starting pressure from which the pressure of the superior-limb cuff is to be decreased, a pressure higher by the prescribed pressure than the estimated systolic blood pressure of the superior limb determined by the estimated-superior-limb-systolic-blood-pressure determining means; and pressure-decrease control means for simultaneously starting decreasing, at a common rate, the respective pressures of the inferior-limb cuff and the superior-limb cuff from the first and second pressure-decrease starting pressures, respectively, so that the respective pressures of the inferior-limb cuff and the superior-limb cuff become equal to the respective estimated systolic blood pressures of the inferior limb and the superior limb, at the same time.

* * * * *